United States Patent [19]

Onishi et al.

[11] Patent Number: 5,777,116

[45] Date of Patent: Jul. 7, 1998

[54] CYCLOPROPANE DERIVATIVES AND METHOD OF PREPARING THE SAME

[75] Inventors: Tomoyuki Onishi; Takashi Tsuji; Toshihiro Matsuzawa, all of Kawasaki, Japan

[73] Assignee: Ajinomoto Co., Inc., Tokyo, Japan

[21] Appl. No.: 648,407

[22] Filed: May 15, 1996

Related U.S. Application Data

[62] Division of Ser. No. 413,226, Mar. 30, 1995, Pat. No. 5,556,994.

[30] Foreign Application Priority Data

Mar. 30, 1994 [JP] Japan ................................. 6-061250
Jul. 27, 1994 [JP] Japan ................................. 6-175495

[51] Int. Cl.$^6$ .................. C07D 473/02; C07D 473/04; C07D 473/06; C07D 473/26
[52] U.S. Cl. .................. 544/264; 544/267; 544/268; 544/277
[58] Field of Search ................... 544/268, 264, 544/267, 277

[56] References Cited

U.S. PATENT DOCUMENTS 5,484,920  1/1996  Suzuki et al. ..................... 544/268
5,532,368  7/1996  Kufner-Muhl et al. ............. 544/267

Primary Examiner—Ba K. Trinh
Attorney, Agent, or Firm—Oblon, Spivak, McClelland, Maier & Neustadt, P.C.

[57] ABSTRACT

A cyclopropane derivative represented by formula (I):

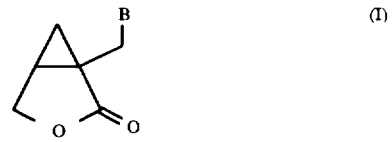

wherein B represents a group of a purine derivative.

Another aspect of the invention provides (3-oxa-2-oxobicyclo[3.1.0]hexan-1-yl)methanol and a method of preparing a cyclopropane derivative of formula (I) from this compound by replacing the hydroxyl group of the compound with a leaving group followed by reaction with a purine derivative.

1 Claim, No Drawings

CYCLOPROPANE DERIVATIVES AND METHOD OF PREPARING THE SAME

This is a division of application Ser. No. 08/413,226 filed on Mar. 30, 1995, now U.S. Pat. No. 5,556,994.

BACKGROUND OF THE INVENTION

1. Field of the Invention

The present invention relates to cyclopropane derivatives which are useful in the preparation of antiviral agents and the like, and to methods of preparing such derivatives and also to the intermediates useful in preparation of such derivatives.

2. Description of the Background

Compounds represented by formula (a) infra are known to have potent antiviral activity (JP-A-5/78357).

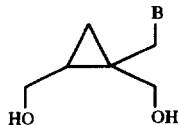
(a)

However, the method described for preparation of these compounds in the above publication is a time-consuming process involving the protection of an intermediate followed by a step of deprotection, and is not suitable for industrial-scale production of the compounds. A need therefore continues to exist for an industrially more advantageous method of producing of the above compounds.

SUMMARY OF THE INVENTION

Accordingly, one object of the invention is to provide a less time consuming industrially acceptable method of preparing a compound of formula (a).

Briefly, this object and other objects of the present invention as hereinafter will become more readily apparent can be attained in a cyclopropane derivative of formula (I) which is useful for preparing the compounds of formula (a) shown above simply and conveniently at a high yield.

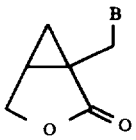
(I)

In the formula B is the radical of a purine derivative.

DETAILED DESCRIPTION OF THE PREFERRED EMBODIMENTS

In formula (I), B may be a guanine residue, an adenine residue, a 2-amino-6-chloropurine residue, an xanthine residue, a hypoxanthine residue, a 2,6-diaminopurine residue or a 2-aminopurine residue, and preferably is guanin-9-yl, 2-amino-6-chloropurin-9-yl, 2-acetoamino-6-chloropurin-9-yl, 2-acetoamino-6-(N,N-diphenylcarbamoyl)oxypurin-9-yl, 2-amino-6-benzyloxypurin-9-yl, 2-amino-6-(methoxyethoxy)purin-9-yl or adenin-9-yl.

The compound of formula (I) according to the present invention may be prepared, for example, by the following reactions:

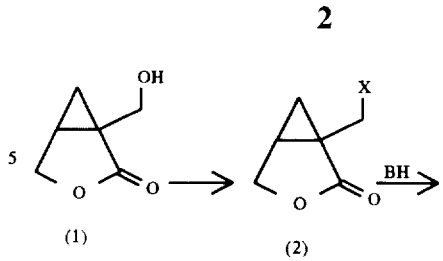
(1) (2)

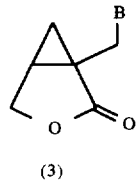
(3)

In formula (a) X represents a leaving group and B is defined as above.

Precisely, the hydroxyl group of compound (1) is converted into a leaving group such as a halogen or a sulfonyloxy group to form compound (2). This compound is then reacted with a purine derivative in the presence of a base such as potassium carbonate to prepare a compound according to the present invention.

When compound (1) is halogenated, it may be reacted with carbon tetrabromide, carbon tetrachloride, bromine or N-bromosuccinimide in the presence of a trialkylphosphine or triphenylphosphine or it is halogenated using a halogenating agent such as thionyl chloride or phosphorus tribromide. Typically, when triphenylphosphine and carbon tetrachloride are employed, 1.1 to 3, preferably 1.2 to 2 equivalents of triphenylphosphine and 1.1 to 100, preferably 1.5 to 5 equivalents of carbon tetrachloride are employed and reacted with the bicyclic compound of formula (1) in a solvent such as dichloromethane, dichloroethane or dimethylformamide at a temperature of −20° to 40° C., preferably 0° to 30° C. for the period of 5 minutes to 3 hours. In such a process, 0.1 to 2 equivalents of a base such as triethylamine or pyridine may be present. When thionyl chloride is used as a halogenating agent, a reaction may be conducted in the presence of 1 to 2 equivalents of a base such as triethylamine or pyridine using 1 to 2 equivalents of thionylchloride in a solvent such as dichloromethane at a temperature of 0° to 50° C. for a period of 5 minutes to 3 hours.

In the case of conversion of the hydroxy group of the compound of formula (1) into a sulfonyloxy group, the reaction may be conducted in the presence of 1 to 2 equivalents of a base such as triethylamine or pyridine using 1 to 2 equivalents of methanesulfonyl chloride or p-toluenesulfonyl chloride in a solvent such as dichloromethane or ethyl acetate at a temperature of 0° to 50° C. for a period of 5 minutes to 10 hours.

The reaction of compound (2) with the likes of a purine derivative may be conducted by adding compound (2) to the purine derivative in the presence of a base such as sodium potassium carbonate or sodium hydride in an amount of 1 to 3, preferably 1 to 1.1 equivalents based on the amount of the purine derivative in a polar solvent such as dimethylformamide, acetonitrile or tetrahydrofuran at a temperature of 0° to 80° C. for a period of 1 to 72 hours. In this process, a crown ether such as 18-crown-6 may be added to facilitate the reaction.

The starting material in the reaction mentioned above, namely, (3-oxa-2-oxobicyclo[3.1.0]hexan-1-yl)methanol (compound (1)) is a novel compound, and may be prepared by the multistep method infra:

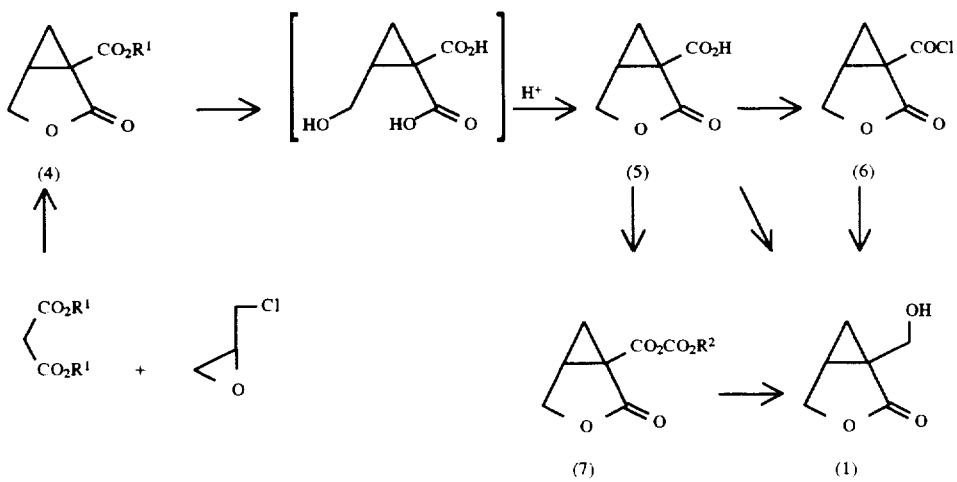

In the formulas $R^1$ represents a lower alkyl group, and $R^2$ represents a lower alkyl or an aryl group.

Compound (4) may be obtained by reacting dialkyl malonate with epichlorohydrin in the presence of a base such as sodium alkoxide by the known method (Helv. Chim. Acta. 72, 1301 (1989)). In this reaction, by using an optically active epichlorohydrin, an optically active compound (4) is obtained and its absolute structure can be retained in compound (1) and compound (3).

Compound (4) can readily be converted into compound (5) by saponification with an alkali such as sodium hydroxide or potassium hydroxide followed by cyclization into a lactone using a suitable acid such as hydrochloric acid or sulfuric acid.

Compound (5) thus obtained leads directly to compound (1) through a reaction with 0.8 to 1.2 equivalents of a reducing agent such as diborane in a polar solvent such as tetrahydrofuran. Alternatively, compound (5) is converted into compound (6) through a reaction with 1 to 10 equivalents of thionyl chloride and then into compound (1) through reaction with 0.5 to 2 equivalents of a reducing agent such as sodium borohydride in a polar solvent such as dioxane or diglyme. Further, alternatively, compound (5) may be converted into compound (7) through a reaction with 1 to 2 equivalents of chloroformate in the presence of 1 to 2 equivalents of a base such as triethylamine or pyridine in a solvent such as tetrahydrofuran and then into compound (1) through reaction with 0.5 to 5 equivalents of a reducing agent such as sodium borohydride.

Another process can be used to obtain compound (1) as follows:

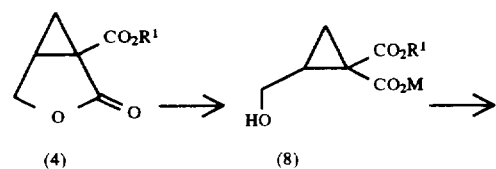

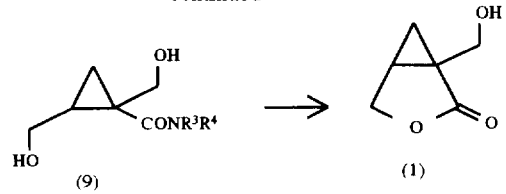

In the formulas above, $R^1$ is defined as above, and $R^3$ and $R^4$ are each hydrogen or an alkyl group.

Compound (4) is reacted with 1 to 10 equivalents of an anine such as ammonia in a solvent such as ethanol or methanol to prepare compound (8), to which 0.5 to 20 equivalents of a reducing agent such as sodium borohydride are added to prepare compound (9). Then the amide is hydrolyzed with a suitable acid such as hydrochloric acid or sulfuric acid to cyclize the lactone ring, thereby preparing compound (1).

Still another alternative method of preparing compound (1) is an follows:

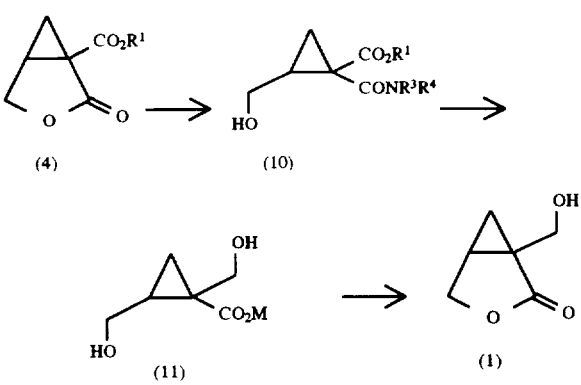

wherein $R^1$ is defined as above and M represents an alkali metal or an alkaline earth metal.

Compound (4) is reacted with 0.8 to 1.2 equivalents of a base such as sodium hydroxide in a solvent such as ethanol or methanol to prepare compound (10), with which 0.5 to 20 equivalents of a reducing agent such as sodium borohydride are reacted to prepare compound (11). Then a suitable acid such as hydrochloric acid or sulfuric acid is added to cyclize the lactone ring to prepare compound (1).

A cyclopropane derivative represented by formula (I) according to the present invention (compound (3)) can be converted into a compound represented by formula (a) (compound (12)) which has potent antiviral activity through a reaction with 0.5 to 20 equivalents of a reducing agent such as sodium borohydride in a suitable solvent such as ethanol, methanol, water or the like.

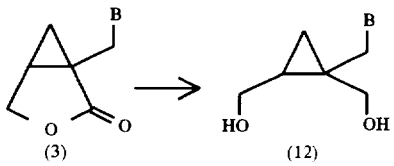

wherein B is defined as above.

When B is 2-amino-6-chloropurine, 2-acetoamino-6-chloropurine, 2-acetoamino-6-(N,N-diphenylcarbamoyl) oxypurine, 2-amino-6-benzyloxypurine or 2-amino-6-(methoxyethoxy)purine or the like, the base moiety can be converted into guanine by an appropriate means such as acid hydrolysis, alkaline hydrolysis and reduction. Conversion into guanine is preferably conducted before the reduction of the lactone ring.

The cyclopropane derivative of formula (I) and its precursor (3-oxa-2-oxobicyclo|3.1.0|hexan-1-yl)methanol include their racemates, optical isomers and stereoisomers. As described above, by using an optically active epichlorohydrin, any of the optical isomers can be prepared similarly as described above. Alternatively, any of the intermediates or the final product may be resolved by optical resolution column chromatography or by fractional crystallization using diastereomeric salts.

Having generally described this invention, a further understanding can be obtained by reference to certain specific examples which are provided herein for purposes of illustration only and are not intended to be limiting unless otherwise specified.

With regard to the relative configuration in the examples, the cyclopropane moiety is considered to be on a flat plane and the substituents positioned below the plane are represented by "α" while those positioned above the same by "β".

EXAMPLE 1

Preparation of (3-oxa-2-oxobicyclo|3.1.0|hexan-1-yl)methanol

Process 1

Preparation of ethyl 3-oxa-2-oxobicyclo|3.1.0|hexan-1-carboxylate

A 2.42 g (105 mmol) amount of metallic sodium was dissolved in 200 ml of ethanol at 0° C. in an argon atmosphere. 16.7 g (110 mmol) of diethyl malonate was added to the solution and then 7.8 ml (100 mmol) of epichlorohydrin dissolved in 5 ml of ethanol was added dropwise at room temperature. The solution thus obtained was heated at 75° C. for 20 hours and then cooled to 0° C. The precipitate which formed was removed by filtration. The filtrate was concentrated under reduced pressure, and water was added to the residue, which was then extracted with dichloromethane. The organic layer was dried over anhydrous sodium sulfate, and the solvent was removed by distillation. The residue was purified by silica gel chromatography (hexane: ethyl acetate=5:1 to 1:1) to yield 12.0 g (70 mmol, 70%) of the above-named compound.

Colorless oil $^1$H-NMR(CDCl$_3$)δ: 1.31(t, J=7.1 Hz, 3H), 1.37(dd, J=4.8, 5.4 Hz, 1H), 2.08(dd, J=4.8, 8.0 Hz, 1H), 2.72(m, 1H), 4.18(d, J=9.6 Hz, 1H), 4.27(q, J=7.1 Hz, 2H), 4.36(dd, J=4.5, 9.6 Hz, 1H)

FD Mass spectrum: 170 (M$^+$)

Process 2

Preparation of 3-oxa-2-oxobicyclo|3.1.0|hexan-1-carboxylic acid

A 5.10 g (30.0 mmol) amount of ethyl 3-oxa-2-oxobicyclo |3.1.0|hexan-1-carboxylate was dissolved in 80 ml of 1N aqueous solution of sodium hydroxide and stirred at room temperature for 4 hours. After the solvent was concentrated to a volume of about 40 ml under reduced pressure, 10 ml of concentrated hydrochloric acid was added to adjust the pH to 1 or lower and the mixture was adsorbed on a resin (SEPABEADS SP-207, Mitsubishi Kasei) equilibrated with 0.1N hydrochloric acid. After washing the resin with 120 ml of 0.1N hydrochloric acid and 80 ml of water, the product was eluted with 300 ml of 20% aqueous solution of methanol to yield 3.85 g (27.0 mmol, 90%) of the above-named compound.

White solid $^1$H-NMR(CDCl$_3$)δ: 1.56(dd, J=4.5, 5.6 Hz, 1H), 2.15(dd, 4.5, 7.8 Hz, 1H), 2.96–3.03(m, 1H), 4.31(d, J=9.6 Hz, 1H), 4.47(dd, J=5.0, 9.6 Hz, 1H)

FAB Mass spectrum: 143 (MH$^+$)

Process 3

Preparation of 3-oxa-2-oxobicyclo|3.1.0|hexan-1-carbonyl chloride

A 134.7 mg (0.948 mmol) amount of 3-oxa-2-oxobicyclo |3.1.0|hexan-1-carboxylic acid was dissolved in 1.13 g of thionyl chloride, and stirred at 65° C. for 100 minutes. After cooling to room temperature, thionyl chloride was distilled off under reduced pressure to obtain 152.2 mg (0.984 mmol, 100%) of the above-named compound.

White solid $^1$H-NMR(CDCl$_3$)δ: 1.68(t, J=5.4 Hz, 1H), 2.41(dd, J=5.4, 8.4 Hz, 1H), 3.04–3.11(m, 1H), 4.24(d,j=9.9 Hz, 1H), 4.44 (dd, J=4.7, 9.9 Hz, 1H)

FAB Mass spectrum: 161 (MH$^+$)

Process 4

Preparation of (3-oxa-2-oxobicyclo|3.1.0|hexan-1-yl) methanol

A 76.1 mg (0.474 mmol) amount of 3-oxa-2-oxobicyclo |3.1.0|hexan-1-carbonyl chloride was dissolved in 2 ml of 1,4-dioxane and 10.8 mg (0.284 mmol) of sodium borohydride was added. After stirring for 3 hours at room temperature, phosphate buffer (pH 7) was added and the mixture was extracted with ethyl acetate. The organic layer was dried over anhydrous sodium sulfate, and then the solvent was distilled off under reduced pressure. The residue was purified by silica gel column chromatography (dichloromethane:methanol=19:1) to yield 15.7 mg (0.123 mmol, 26%) of the above-named compound.

Colorless oil $^1$H-NMR(CDCl$_3$)δ: 1.01(t, J=4.8 Hz, 1H), 1.32(dd, J=4.8, 7.7 Hz, 1H), 2.26–2.33(m, 1H), 3.69(d, 12.6 Hz, 1H), 4.05(d, J=12.6 Hz, 1H), 4.18(d, J=9.3 Hz, 1H), 4.34(dd, J=4.7, 9.3 Hz, 1H)

FAB Mass spectrum: 129 (MH$^+$)

EXAMPLE 2

Preparation of (3-oxa-2-oxobicyclo|3.1.0|hexan-1-yl) methanol

A 72.5 mg (0.510 mmol) amount of 3-oxa-2-oxobicyclo |3.1.0|hexan-1-carboxylic acid and 77.4 mg (0.764 mmol) of triethylamine were dissolved in 1.0 ml of tetrahydrofuran and cooled to −18° C., and then 83.0 mg (0.764 mmol) of ethyl chloroformate in 0.5 ml of tetrahydrofuran was added. After stirring for 30 minutes at −18° C., 57.9 mg (1.53 mmol) of sodium borohydride in 0.75 ml of water was added. After further stirring for 20 minutes at −18° C., 2 ml of 2N hydrochloric acid were added. Tetrahydrofuran was distilled off under reduced pressure, and the residue was extracted with dichloromethane. After drying the organic layer over anhydrous sodium sulfate, the solvent was distilled off under reduced pressure. The residue was purified by silica gel column chromatography (dichloromethane:methanol=19:1) to yield 35.9 mg (0.281 mmol, 55%) of the above-named compound. This compound had physical data similar to that of Example 1.

EXAMPLE 3

Preparation of (3-oxa-2-oxobicyclo(3.1.0)hexan-1-yl) methanol

Process 1

Preparation of 1β-ethoxycarbonyl-2α-hydroxymethylcyclopropan-1-carboxyamide

A 1.73 q (10.2 mmol) amount of ethyl 3-oxa-2-oxobicyclo |3.1.0|hexan-1-carboxylate was dissolved in 2M $NH_3$/methanol solution. After stirring at room temperature for 15 minutes, the solvent was distilled off under reduced pressure. The residue was purified by silica gel column chromatography (ethyl acetate) to obtain 1.12 q (6.62 mmol, 65%) of the above-named compound.

White solid $^1$H-NMR($CDCl_3$)δ: 1.25(t, J=7.1 Hz, 1H), 1.80(dd, 4.5, 9.7 Hz, 1H), 1.86(dd, 4.5, 8.0 Hz, 1H), 2.19–2.30(m, 1H), 3.67–3.78(m, 1H), 3.90–3.99(m 1H),4.15(q, J=7.1 Hz, 2H), 5.96(bs, 1H), 8.25(bs, 1H)

FAB mass spectrum: 188 ($MH^+$)

Process 2

Preparation of 1β,2α-bis(hydroxymethyl)cyclopropan-1-carboxyamide

A 94.9 mg (0.558 mmol) amount of 1β-ethoxycarbonyl-2α-hydroxyrethylcyclopropan-1-carboxyamide was dissolved in 1.2 ml of t-butyl alcohol and 42.2 mg (0.558 mmol) of sodium borohydride was added. After heating to 83° C., 0.2 ml of methanol was added and the mixture was heated under reflux for 1 hour. After cooling to room temperature, 0.279 ml of 2N hydrochloric acid was added and the solvent was distilled off under reduced pressure. The residue was purified by silica gel column chromatography (dichloromethane : methanol=9:1) to yield 70.3 mg (0.485 mmol, 87%) of the above-named compound.

Colorless oil $^1$H-NMR($CD_3OD$)δ: 0.88(dd, J=4.9, 8.9 Hz, 1H), 1.24 (dd, J=4.9, 6.3 Hz, 1H), 1.40–1.50(m, 1H), 3.50(d, J=12.0 Hz, 1H), 3.61(dd, J=7.4, 11.7 Hz, 1H), 3.66(dd, J=6.9, 11.7 Hz, 1H), 3.76(d, J=12.0 Hz, 1H)

FAB mass spectrum: 146 ($MH^+$)

Process 3

Preparation of (3-oxa-2-oxobicyclo|3.1.0|hexan-1-yl) methanol

A 31.0 mg (0.214 mmol) amount of 1β,2α-bis(hydroxymethyl)cyclopropan-1-carboxyamide was admixed with 2.1 ml of 2N hydrochloric acid. After stirring at room temperature for 18 hours, 8.4 ml of water was added and the mixture was extracted with ethyl acetate. After drying the organic layer over anhydrous sodium sulfate, the solvent was distilled off under reduced pressure. The residue was purified by silica gel column chromatography (dichloromethane:methanol=19:1) to yield 23.1 mg (0.166 mmol, 78%) of the above-named compound. This compound had physical data similar to that of Example 1.

EXAMPLE 4

Preparation of (3-oxa-2-oxobicyclo|3.1.0|hexan-1-yl) methanol

A 258.7 mg (1.52 mmol) amount of ethyl 3-oxa-2-oxobicyclo|3.1.0|hexan-1-carboxylate was dissolved in 5 ml of ethanol and 60.8 mg (1.52 mmol) of sodium hydroxide in 5 ml of ethanol was added. After stirring for 16 hours, 287.5 mg (7.60 mmol) of sodium borohydride was added and the mixture was heated under reflux for 3 hours. After cooling to room temperature, 4.56 ml of 2N hydrochloric acid was added. After distilling ethanol off under reduced pressure, 10 ml of 2N hydrochloric acid was further added. After stirring for 18 hours, the mixture was extracted with ethyl acetate. After drying the organic layer over anhydrous sodium sulfate, the solvent was distilled off under reduced pressure. The residue was purified by silica gel column chromatography (dichloromethane:methanol=19:1) to yield 106.2 mg (0.829 mmol, 55%) of the above-named compound. This compound had physical data similar to that of Example 1.

EXAMPLE 5

Preparation of 2-amino-6-chloro-9-(3'-oxa-2'-oxobicyclo|3.1.0|hexan-1'-yl)methylpurine

Process 1

Preparation of (3-oxa-2-oxobicyclo|3.1.0|hexan-1-yl) methyl bromide

A 15.7 mg (0.123 mmol) amount of (3-oxa-2-oxobicyclo |3.1.0|hexan-1-yl)methanol, 6.2 mg (0.062 mmol) of triethylamine and 58.1 mg (0.221 mmol) of triphenylphosphine were dissolved in 1.5 ml of dichloromethane, and the mixture was cooled to 0° C. and then 73.4 mg (0.221 mmol) of carbon tetrabromide was added. After stirring for 100 minutes, phosphate buffer (pH 7) was added and the mixture was extracted with dichloromethane. After drying the organic layer over anhydrous sodium sulfate, the solvent was distilled off under reduced pressure. The residue was purified by silica gel column chromatography (hexane:ethyl acetate=5:1) to yield 13.3 mg (70 μmol, 57%) of the above-named compound.

White solid $^1$H-NMR($CDCl_3$)δ: 1.28(t, J=5.1 Hz, 1H), 1.49(dd, J=5.1, 7.8 Hz, 1H), 2.33–2.40(m, 1H), 3.30(d, J=11.3 Hz, 1H), 4.12(d, J=11.3 Hz, 1H), 4.17(d, J=9.3 Hz, 1H), 4.36(dd, J=4.7, 9.3 Hz, 1H)

Process 2

Preparation of 2-amino-6-chloro-9-(3'-oxa-2'-oxobicyclo|3.1.0|hexan-1'-yl)methylpurine A 13.3 mg (69.6 μmol) amount of (3-oxa-2-oxobicyclo |3.1.0|hexan-1-yl)methyl bromide was dissolved in 1.4 ml of N,N-dimethylformamide and 11.8 mg (69.6 μmol) of 2-amino-6-chloropurine and 9.6 mg (69.6 μmol) of potassium carbonate were added. After stirring for 17 hours at room temperature, insoluble materials were filtered off, and the filtrate was distilled off under reduced pressure. The residue was purified by silica gel column chromatography (dichloromethane:methanol=49:1) to yield 11.4 mg (41.1 μmol 59%) of the above-named compound.

White solid

¹H-NMR(CD₃OD)δ: 1.16(t, J=4.8 Hz, 1H), 1.65(dd, J=4.8, 7.8 Hz, 1H), 2.70–2.76(m, 1H), 4.20(d, J=9.3 Hz, 1H), 4.29(dd, J=4.5, 9.3 Hz, 1H), 4.37(d, J=15.0 Hz, 1H), 4.69(d, J=15.0 Hz, 1H), 8.17(s, 1H)

FAB mass spectrum: 280 (MH⁺)

EXAMPLE 6

Preparation of 2-amino-6-chloro-9-(3'-oxa-2'-oxobicyclo[3,1,0]hexan-1'-yl)methylpurine

Process 1

Preparation of (3-oxa-2-oxobicyclo[3,1,0]hexan-1-yl) methyl chloride

A 31.3 mg (0.244 mmol) amount of (3-oxa-2-oxobicyclo[3,1,0]hexan-1-yl)methanol and 37.0 mg (0.366 mmol) of triethylamine were dissolved in 1 ml of dichloromethane, and then 43.5 mg (0.366 mmol) of thionyl chloride in 1 ml of dichloromethane was added. After stirring for 90 minutes, phosphate buffer (pH 7) was added and the solvent was distilled off under reduced pressure. The residue was purified by silica gel column chromatography (hexane:ethyl acetate=2:1) to yield 29.5 mg (0.200 mmol, 82%) of the above-named compound.

White solid

¹H-NMR(CDCl₃)δ: 1.16(t, J=5.1 Hz, 1H), 1.47(dd, J=5.1, 8.0 Hz,, 1H), 2.35–2.42(m, 1H), 3.48(d, J=12.0 Hz, 1H), 4.19(d, J=9.3 Hz, 1H), 4.27(d, J=12.0 Hz, 1H), 4.36(dd, J=4.5, 9.3 HZ, 1H)

Process 2

Preparation of 2-amino-6-chloro-9-(3'-oxa-2'-oxobicyclo[3,1,0]hexan-1'-yl)methylpurine A 27.8 mg (0.190 mmol) amount of (3-oxa-2-oxobicyclo[3,1,0]hexan-1-yl)methyl chloride was dissolved in 1.9 ml of N,N-dimethylformamide and 32.2 mg (0.19 mmol) of 2-amino-6-chloropurine and 26.3 mg (0.190 mmol) of potassium carbonate were added. After stirring for 21 hours at room temperature, stirring was further continued at 55° C. for 20 hours. Insoluble materials were filtered off, and the filtrate was concentrated under reduced pressure. The residue was purified by silica gal column chromatography (dichloromethane:methanol=49:1) to yield 41.5 mg (0.148 mmol, 78%) of the above-named compound. This compound had physical data similar to that of example 5.

EXAMPLE 7

Preparation of 2-amino-6-chloro-9-(3'-oxa-2'-oxobicyclo[3,1,0]hexan-1'-yl)methylpurine

Process 1

Preparation of (3-oxa-2-oxobicyclo[3,1,0]hexan-1-yl) methyl methanesulfonate

A 33.0 mg (0.258 mmol) amount of (3-oxa-2-oxobicyclo[3,1,0]hexan-1-yl)methanol and 39.1 mg (0.386 mmol) of triethylamine were dissolved in 1 ml of dichloromethane and cooled to 0° C., and then 35.5 mg (0.310 mmol) of methanesulfonyl chloride in 1 ml of dichloromethane was added. After stirring for 21 hours, phosphtate buffer (pH 7) was added and the mixture was extracted with dichloromethane. After drying the organic layer over anhydrous sodium sulfate, the solvent was distilled off under reduced pressure. The residue was purified by silica gal column chromatography (hexane:ethyl acetate=1:1) to yield 35.5 mg (0.173 mmol, 67%) of the above-named compound.

White solid

¹H-NMR(CDCl₃)δ: 1.16(t, J=5.1 Hz, 1H), 1.44(dd, J=5.1, 8.0 Hz, 1H), 2.47–2.54(m, 1H), 3.08(s, 3H), 4.13(d, J=11.9 Hz, 1H), 4.21(d, J=9.3 Hz, 1H), 4.38(dd, J=4.8, 9.3 Hz, 1H), 4.87(d, J=11.9 Hz, 1H)

Process 2

Preparation of 2-amino-6-chloro-9-(3'-oxa-2'-oxobicyclo[3,1,0]hexan-1'-yl)methylpurine A 35.5 mg (0.172 mmol) amount of (3-oxa-2-oxobicyclo[3,1,0]hexan-1-yl)methyl methanesulfonate was dissolved in 1.7 ml of N,N-dimethylformamide and 29.2 mg (0.172 mmol) of 2-amino-6-chloropurine and 23.8 mg (0.172 mmol) of potassium carbonate were added. After stirring for 20 hours at room temperature, insoluble materials were filtered off, and the filtrate was distilled under reduced pressure. The residue was purified by silica gel column chromatography (dichloromethane:methanol=49:1) to yield 37.5 mg (0.134 mmol, 78%) of the above-named compound. This compound had physical data similar to that of Example 5.

EXAMPLE 8

Preparation of 9-(3'-oxa-2'-oxobicyclo[3,1,0]hexan-1'-yl) methylguanine

A 11.7 mg (41.8 μmol) amount of 2-amino-6-chloro-9-(3'-oxa-2'-oxobicyclo[3,1,0]hexan-1'-yl)methylpurine was dissolved in 0.5 ml of 80% formic acid and the solution was heated at 100° C. for 2 hours. After cooling to room temperature, the solvent was distilled off under reduced pressure. After adjustment of the pH to 4 with potassium carbonate followed by purification by reverse C18 silica gel chromatography (water:methanol=3:1), 10.9 mg (41.8 μmol, 100%) of the above-named compound were obtained.

White solid

¹H-NMR(DMSO-d₆)δ: 1.05(t, J=4.8 Hz, 1H), 1.42(dd, J=4.8, 7.8 Hz, 1H), 2.57–2.64(m, 1H), 4.11(d, J=9.3 Hz, 1H), 4.13(d, J=14.9 Hz, 1H), 4.25(dd, J=4.5, 9.3 Hz, 1H), 4.44(d, J=14.9 Hz, 1H), 6.41(bs, 2H), 7.66(s, 1H)

High resolution mass spectrum ($C_{11}H_{12}O_3N_5$, M⁺+H):

Calculated value: 262.0940

Found value: 262.0942

EXAMPLE 9

Preparation of 9-[1'α, 2'α-bis(hydroxymethyl)cyclopropan-1'-yl]methylguanine

A 20.9 mg (80.0 μmol) amount of 9-(3'-oxa-2'-oxobicyclo[3,1,0]hexan-1'-yl)methylguanine was dissolved in 1 ml of ethanol, and 15.1 mg (0.400 mmol) of sodium borohydride was added. After stirring at 80° C. for 90 minutes, 0.25 ml of 2N hydrochloric acid was added and ethanol was distilled off under reduced pressure. After adjustment of the pH to 4 with potassium carbonate followed by purification by reverse C18 silica gel chromatography (water:methanol=4:1), 19.7 mg (74.4 μmol, 93%) of the above-named compound were obtained.

White solid

¹H-NMR(DMSO-d₆)δ: 0.40(t, J=5.1 Hz, 1H), 0.88(dd, J=4.8, 8.7 Hz, 1H), 1.23(m, 1H), 3.24–3.37(m, 2H), 3.41(dd, J=6.0, 12.0 Hz, 1H), 3.58(dt, J=12.0, 6.0 Hz, 1H), 3.81(d, J=14.1 Hz, 1H), 4.00(d, J=14.1 Hz, 1H), 4.49(m, 1H), 4.64(m, 1H), 6.38(bs, 2H), 7.71(s, 1H), 10.49(bs, 1H)

High resolution mass spectrum $C_{11}H_{16}O_3N_5$, M⁺+H):

Calculated value: 266.1253

Found value: 266.1263

EXAMPLE 10

Preparation of 9-(3'-oxa-2'-oxobicyclo[3,1,0]hexan-1'-yl] methyladenine

A 40.0 mg (1.00 mmol) amount of 60% sodium hydride which had previously been washed with hexane were suspended in 10 ml of N,N-dimethylformamide, and 210.5 mg (1.02 mmol) of (3-oxa-2-oxobicyclo[3.1.0]hexan-1-yl) methyl methanesulfonate and 135.1 mg (1.00 mmol) of adenine were added. After stirring at 60° C. for 3 hours, insoluble materials were filtered off, and the filtrate was distilled under reduced pressure. The residue was purified by silica gel column chromatography (dichloromethane:methanol=19:1) to yield 153.0 mg (0.624 mmol, 62%) of the above-named compound.

White solid $^1$H-NMR(DMSO-d$_6$)δ: 1.06(t, J=4.7 Hz, 1H), 1.54(dd, J=4.7, 7.8 Hz, 1H), 2.59–2.67(m, 1H), 4.10(d, J=9.3 Hz, 1H), 4.22(dd, J=5.0, 9.3 Hz, 1H), 4.37(d, J=15.0 Hz, 1H), 4.63(d, J=15.0 Hz, 1H), 7.20(bs, 2H), 8.10(s, 1H), 8.14(s, 1H)

High resolution mass spectrum ($C_{11}H_{12}O_2N_5$, M$^+$+H):
Calculated value: 246.0991
Found value: 246.0993

EXAMPLE 11

Preparation of 9-[1'α,2'α-bis(hydroxymethyl)cyclopropan-1'-yl]methyladenine

A 36.1 mg (0.147 mmol) amount of 9-(3'-oxa-2'-oxobicyclo[3.1.0]hexan-1'-yl)methyladenine was dissolved in 1.5 ml of ethanol, and 27.8 mg (0.736 mmol) of sodium borohydride was added. After stirring at room temperature for 14 hours, 0.37 ml of 2N hydrochloric acid was added and ethanol was distilled off under reduced pressure. After adjustment of the pH to 4 followed by the purification by reverse C18 silica gel chromatography (water:methanol= 4:1), 33.3 mg (0.134 mmol, 91%) of the above-named compound were obtained.

White solid $^1$H-NMR(DMSO-d$_6$)δ: 0.41(t, J=5.1 Hz, 1H), 0.93(dd, J=5.1, 8.7 Hz, 1H), 1.32(m, 1H), 3.23–3.44(m, 3H), 3.58(m, 1H), 4.02(d, J=14.2 Hz, 1H), 4.19(d, J=14.2 Hz, 1H), 4.56(d, J=5.2 Hz, 1H), 4.74(d, J=5.2 Hz, 1H), 7.20(bs, 2H), 8.13(s, 1H), 8.16(s, 1H)

High resolution mass spectrum ($C_{11}H_{16}O_2N_5$, M$^+$+H):
Calculated value: 250.1304
Found value: 250.1310

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A cyclopropane derivative represented by formula (I):

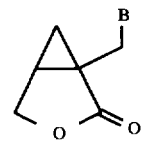

(I)

wherein B is guanin-9-yl, 2-amino-6-chloropurin-9-yl, xanthin-9-yl, hypoxanthin-9-yl, 2,6-diaminopurin-9-yl, 2-acetoamino-6-2-aminopurin-9-yl chloropurin-9-yl, 2-acetoamino-6-N,N-diphenylcarbamoyl)oxypurin-9-yl, 2-amino-6-benzyloxypurin-9-yl, 2-amino-6-(methoxyethoxy)purin-9-yl or adenin-9-yl.

* * * * *